(12) United States Patent
Reid et al.

(10) Patent No.: US 8,034,777 B2
(45) Date of Patent: Oct. 11, 2011

(54) MODIFIED ANTICHOLINERGIC NEUROTOXINS AS MODULATORS OF THE AUTOIMMUNE REACTION

(75) Inventors: Paul F. Reid, Plantation, FL (US); Laurence N. Raymond, Plantation, FL (US)

(73) Assignee: Receptopharm, Inc., Plantation, FL (US)

( * ) Notice: Subject to any disclaimer, the term of this patent is extended or adjusted under 35 U.S.C. 154(b) by 425 days.

(21) Appl. No.: 10/947,434

(22) Filed: Sep. 23, 2004

(65) Prior Publication Data

US 2006/0062776 A1    Mar. 23, 2006

(51) Int. Cl.
*A61K 38/00*    (2006.01)

(52) U.S. Cl. ..... 514/17.9; 514/1.1; 514/21.4; 514/21.92

(58) Field of Classification Search .............. None
See application file for complete search history.

(56) References Cited

U.S. PATENT DOCUMENTS

| | | | | |
|---|---|---|---|---|
| 3,624,218 | A * | 11/1971 | Regelson | 424/78.19 |
| 3,888,977 | A | 6/1975 | Sanders | |
| 4,113,858 | A * | 9/1978 | Hashim | 514/13 |
| 4,126,676 | A | 11/1978 | Sanders | |
| 4,162,303 | A | 7/1979 | Sanders | |
| 4,341,762 | A | 7/1982 | Haast | |
| 4,741,902 | A | 5/1988 | Haast | |
| 5,989,803 | A * | 11/1999 | Tabas et al. | 435/4 |
| 5,989,857 | A | 11/1999 | Mundschenk | |
| 2005/0069525 | A1 * | 3/2005 | Mikael | 424/93.7 |

OTHER PUBLICATIONS

"Saline." Available online at http://www.merriam-webster.com/medlineplus/saline. Accessed Mar. 25, 2010. 1 page.*
Yourist, J.E., Haines, H.G. and Miller K.D., Inhibition of Herpes Simplex Virus Replication by Cobra Alpha-Neurotoxoid, J. Gen Virol. 64:1475-1481 (1983).
Hudson, R.A., Montgomery, I.N. and Rauch H.C., Experimental Allergic Encephalomyelitis: Prevention With a Nontoxic Derivative of a Cobra Neurotoxin, Mol. Immunol. 20(2):229-232 (1983).
Miller, K., Miller G.G., Sanders M. and Fellowes O.N., Inhibition of Virus-Induced Plaque Formation by Atoxic Derivatives of Purified Cobra Neurotoxins, Biophys. et Biophysica Acta 496:192-196 (1977).
Montsdeoca, G. and Stoik, R., Human Clinical Trials on the Effect of Pepteron for Rheumatoid Arthritis, Soc. Exp. Biol. Med., S.E. Sect., vol. 10, p. 9 (1985).
Sanders M. and Fellowes O., Use of Detoxified Snake Neurotoxin as a Partial Treatment for Amyotrophic Lateral Sclerosis, Cancer Cytology 15(2):11-16 (1975).

* cited by examiner

*Primary Examiner* — Lora E Barnhart
(74) *Attorney, Agent, or Firm* — McLaren Legal Services; Margaret J. McLaren, Esq.

(57) ABSTRACT

The invention comprises a composition of matter and method of its use for the treatment of multiple sclerosis in humans. The composition is a modified anticholinergic alpha-neurotoxin. Alpha-neurotoxin solution, such as cobratoxin, is filter sterilized to remove bacteria. It is modified using $H_2O_2$. Any suitable preservative for parenteral administration can be employed such as methyl paraben, benzalkonium chloride or metacreosol. It is preferred that the composition is administered every other day or daily. The composition may be administered orally, subcutaneously, intramuscularly or intravenously. Parenterally, either subcutaneous or intramuscular injection is preferred.

7 Claims, 3 Drawing Sheets

MODIFIED ANTICHOLINERGIC NEUROTOXINS AS MODULATORS OF THE AUTOIMMUNE REACTION

BACKGROUND OF THE INVENTION

1. Field of the Invention

The present invention relates to a class of proteins, and a method for treatment of autoimmune diseases, especially to the treatment of heretofore intractable diseases such as multiple sclerosis, myasthenia gravis, and rheumatoid arthritis through modulation of the immune system reaction. The composition is comprised of a modified anticholinergic alpha-neurotoxin.

2. Description of the Prior Art

Sanders et al. had commenced investigating the application of modified venoms to the treatment of Amyotrophic Lateral Sclerosis (ALS) in 1953 having employed poliomyelitis infection in monkeys as a model. Others antiviral studies had reported inhibition of pseudo rabies (a herpes virus) and Semliki Forest virus (alpha-virus). See Sanders' U.S. Pat. Nos. 3,888,977, 4,126,676, and 4,162,303. Sanders justified the pursuit of this line of research through reference to the studies of Lamb and Hunter (1904) though it is believed that the original idea was postulated by Haast. See Haast U.S. Pat. Nos. 4,341,762 and 4,741,902. The studies of Lamb and Hunter (Lancet 1:20, 1904) showed by histopathologic experiments with primates killed by neurotoxic Indian cobra venom that essentially all of the motor nerve cells in the central nervous system were involved by this venom. A basis of Sanders' invention was the discovery that such neurotropic snake venom, in an essentially non-toxic state, also could reach that same broad spectrum of motor nerve cells and block or interfere with invading pathogenic bacteria, viruses or proteins with potentially deleterious functions. Thus, the snake venom used in producing the composition was a neurotoxic venom, i.e. causing death through neuromuscular blockade. As the dosages of venom required to block the nerve cell receptors would have been far more than sufficient to quickly kill the patient, it was imperative that the venom was detoxified. The detoxified but undenatured venom was referred to as being neurotropic. The venom was preferably detoxified in the mildest and most gentle manner. While various detoxification procedures were known then to the art, such as treatment with formaldehyde, fluorescein dyes, ultraviolet light, ozone or heat, it was preferred that gentle oxygenation at relatively low temperatures be practiced, although the particular detoxification procedure was not defined as critical. Sanders employed a modified Boquet detoxification procedure using hydrogen peroxide (Boquet 1941), outlined below. The acceptability of any particular detoxification procedure was tested by the classical Semliki Forest virus test, as taught by Sanders, U.S. Pat. No. 4,162,303.

From 1972 to 1974, 113 patients were treated for ALS with the crude venom extract without reports of toxicity problems or other adverse reactions (Sanders, M. and Fellowes, 1975). The general cause of ALS has eluded scientists for decades though in a small proportion of that population it has been attributed to a defective cellular enzyme. The objective of the treatment was an attempt to decelerate, stabilize or possibly reverse the progression of the disease.

During that period, a product derived from oxidatively detoxified whole venoms (cobra and krait) was employed as a therapeutic agent in over 1,100 patients with ALS with the longest treated patients receiving treatment for over 12 years. The venom complex contained many potentially active components though the emphasis of research efforts have focused on the neurotoxic fraction. It is unknown what components of the venom were responsible for any benefits reported by Sanders. In patents issued to Haast, it was suggested that a combination of neurotoxins and an unknown component of viperid venom were required. (Sanders did not employ a viperid venom component). Haast employed native, unmodified venom fractions the administration of which was reported to cause quite extensive pain for 1-2 days post administration resulting often in short therapeutic periods even if the reported effects were quite dramatic.

The production of drug product by Dr. M. Sanders was achieved using hydrogen peroxide as the oxidizing agent in addition to other components giving rise to the recipe he employed for over 30 years (Sanders et al., 1975, 1978). This method was patented and published by Sanders on several occasions with the last patent expiring in 1994. Furthermore, several techniques have been developed for modifying neurotoxins. These have included hydrogen peroxide, ozone, performic acid, iodoacetamide and iodoacetic acid. Some of these procedures have been published and others patented. Obviously some procedures are easier than others to utilize and the focus for commercial production has been on the simpler methods.

SUMMARY OF THE INVENTION

It is an object of the invention to provide a method for treating autoimmune diseases, such as multiple sclerosis, myasthenia gravis, rheumatoid arthritis and the like.

It is a further object of the invention to provide a therapy for the treatment of diseases of the aforementioned type, which therapy is safe, effective and may be administered over long periods of time.

Figure 1:
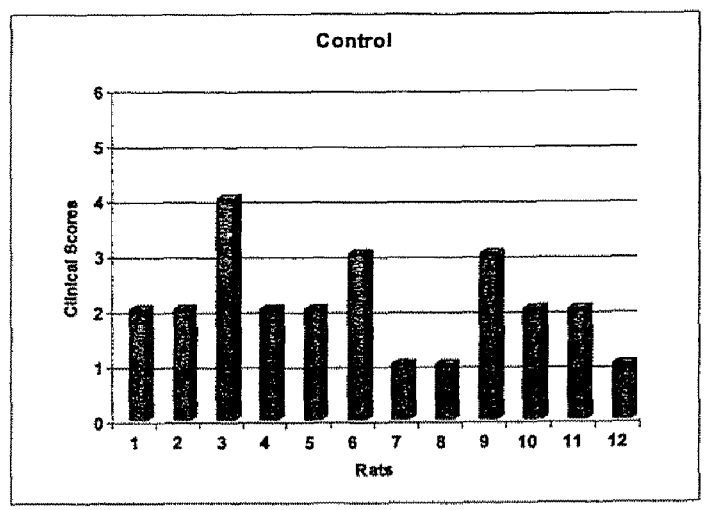
FIG. 1 is a bar graph showing clinical scores achieved by individual rats (Control, Acute Phase) after EAE (experimental acute encephalitis) induction.

Other objects will be apparent to those skilled in the art from the following disclosures and appended claims.

The present invention accomplishes the above-stated objectives, as well as others, as may be determined by a fair reading and interpretation of the entire specification.

In accordance with a principal aspect of the present invention there disclosed a modified and detoxified anticholinergic neurotoxic peptide that can suppress and prevent the onset of a T-cell mediated autoimmune reaction. The invention has application to the treatment of certain human autoimmune diseases, including especially multiple sclerosis, myasthenia gravis, and rheumatoid arthritis.

DETAILED DESCRIPTION OF THE INVENTION

As required, detailed embodiments of the present invention are disclosed herein; however, it is to be understood that the disclosed embodiments are merely exemplary of the invention which may be embodied in various forms. Therefore, specific functional details disclosed herein are not to be interpreted as limiting, but merely as a basis for the claims to be later appended and as a representative basis for teaching one skilled in the art to variously employ the present invention in virtually any appropriate circumstance.

An autoimmune disease results from the immune system's recognition of host structures as foreign and mounts a response to them. What triggers these events is not entirely clear and external factors or events are suspected to be involved. Many infectious agents have epitopes that mimic host structures and autoimmune reactions often occur following a viral or bacterial illness. The cause of some autoimmune diseases are not clearly understood as exemplified by multiple sclerosis, an autoimmune disease of the central nervous system and adult onset diabetes. Others are more clearly defined such as the involvement of the acetylcholine receptor in myasthenia gravis. For some, there is a genetic predisposition to the development of autoimmune disease (rheumatoid arthritis) and in some cases it may arise as a result of immune dysfunction when the immune reaction fails to be down-regulated following clearance of an infectious agent. This type of immune dysfunction is usually attributed to viral infections possibly giving rise to such diseases as systemic lupus erythematosus and chronic fatigue syndrome.

Alpha-cobratoxin is an anticholinergic. Anticholinergics are those drugs which antagonize the activity of acetylcholine and several have been used to treat the symptoms of a number of diseases. Acetylcholine is the major excitatory neurotransmitter of the parasympathetic nervous system including the peripheral nervous system. As antagonists of the acetylcholine receptor both alpha cobratoxin and alpha-bungarotoxin (alpha-neurotoxins) have found great utility as molecular probes in the study of neuro-muscular transmission and ion channel function.

Eight different types of nicotinic acetylcholine receptors (nAchR's) have been identified with variable pharmacological profiles. A homologue, kappa-bungarotoxin, has a higher affinity for neuronal species of acetylcholine receptors. Other alpha-neurotoxins have been isolated from related species of snakes and fish-eating sea snails (Conus geographus, textilis, imperialis and striatus). Cobratoxin and alpha-bungarotoxin have highest affinity for nAchRs containing the alpha 1 and 7 subunits (for a review see Lucas, 1995). In the peripheral nervous system (PNS), the post synaptic response of nicotinic agonists is not blocked by alpha-bungarotoxin and alpha-bungarotoxin binding sites are located extra-synaptically and have a high permeability to calcium (Colquhoun and Patrick, 1997). The toxicity of these molecules is based upon their relative affinity for the receptor which far exceeds that of acetylcholine. Many studies (Miller et al., 1977, Hudson et al., 1983, Lentz et al., 1987, Donnelly-Roberts and Lentz, 1989, Chang et al., 1990, Fiordalisi et al., 1994) have demonstrated various methods for the chemical modification of cobratoxin, by oxidation with substances such as hydrogen peroxide, formalin and ozone, which result in an alteration in affinity for the acetylcholine receptor (AchR) and a concomitant loss in toxicity.

Cobratoxin and one of its homologues, bungarotoxin (BTX), target the nicotinic acetylcholine receptor (nAchR) in nerve and muscle tissue and functions by preventing depolarization of post-synaptic membranes through the regulation of ion channels. Cobratoxin (CTX) has a molecular weight of 7831 and is composed of 71 amino acids. It has no enzymatic activity (like botulinum, tetanus or ricin). It is toxic by virtue of its affinity for the acetylcholine receptor. Many such neurotoxins are very basic in nature, containing large numbers of such residues as lysine and arginine. Binding to the specific target is mediated primarily through electrostatic interactions of amide groups on the toxin to carboxyl groups on the receptor. High salt concentrations can interfere with such interactions. The structure of the protein has been determined by NMR and is composed mostly of antiparallel beta-sheets and random coil. These sheets form three loops, the central loop (loop two) being essential for the protein's activity. Loop two contains the arginine-glycine motif, which is essential for the binding of alpha-neurotoxins. Shortened peptides (10 to 20 mers) composed of residues from loop two can bind to the nAchR, though with lowered affinity, and prevent the activation of the receptors associated sodium channel. It should be noted that there are alpha-neurotoxin binding structures that are not acetylcholine receptors.

The administration of a highly toxic substance such as cobratoxin for therapeutic purposes is fraught with obvious difficulties, even when highly diluted. As a diluted substance, its potential effectiveness is reduced. As taught by Sanders, removal of the toxicity of cobratoxin can be achieved by exposure to heat, formalin, hydrogen peroxide, performic acid, ozone or other oxidizing/reducing agents. The result of exposure of cobratoxin to these agents is the modification of amino acids as well as the possible lysis of one or more disulfide bonds. Tu (1973) has demonstrated that the curaremimetic alpha neurotoxins of cobra and krait venoms lose their toxicity upon either oxidation or reduction and alkylation of the disulfide bonds which has been confirmed by Hudson et al (1983). Loss of toxicity can be determined by the intraperitoneal injection of excess levels of the modified cobratoxin into mice; in general a 0.5 ml volume containing 0.5-1 mg of modified cobratoxin is tested, which represents a minimum of a 400-fold reduction of toxicity. Alternatively, loss of toxicity can be evaluated by depression of binding of the modified neurotoxin to acetylcholine receptors (AchR) in vitro.

Modified cobra venom and cobratoxin in their oxidized (modified or non-toxic) forms have demonstrated antiviral activities. Native cobratoxin and formaldehyde-treated cobratoxin reportedly lack this activity (Miller et al., 1977). The mechanism by which this modified neurotoxin exerts this capacity is not clear as many viruses employ a variety cell surface receptors as portals for entry into the cell prior to replication. Hudson et al. (1983) reported that cobratoxin subjected to alkylation would inhibit the onset of experimental acute encephalitis (EAE) in guinea pigs, a model for multiple sclerosis. EAE is a T-cell mediated autoimmune disease and the study was undertaken as sequence homology was noted between cobratoxin and myelin basic protein (MBP), the protein used to induce the disease. Concerns over possible reversion to toxicity in-vivo by cobratoxin stalled further development though no toxicity was observed over the 3-week study. Recently, modified alpha-cobratoxin has been shown to inhibit the replication of the human immunodeficiency virus (HIV) in peripheral blood mononuclear cells (PBMC's) suggesting the ability of the protein to influence events within immune cells. The mechanism of action is unclear save to say that there is no direct effect on the virus and there is an event at the cell surface that renders the cell resistant to viral infection. This conclusion is drawn from the fact the pretreatment of the immune cells with modified cobratoxin followed by removal of the drug still results in reduced viral replication. This characteristic is also maintained in cells reportedly devoid of acetylcholine receptors.

Human "T" lymphocytes are a major source for acetylcholine (Ach) (Fujii and Kawashima, 2001; Sato et al., 1999; Kawashima et al., 1998; Fujii et al., 1996). Additionally, there is a substantial body of work indicating the presence of both muscarinic AchR's (mAchR's) and nAchR's on the surface of human peripheral blood mononuclear cells (PBMC's) (Fujii and Kawashima, 2001; Singh et al., 2000; Kawashima and Fujii, 2000). Messenger RNA expression of subunits for both nAchR ($\alpha 2$-$\alpha 7$ and $\alpha 2$-$\alpha 4$) and mAchR (m1-m5) was determined for human PBMC indicating the presence of AchR on the cell surface (Sato et al., 1999). Stimulation of T lymphocytes with the mitogen phytohemagglutinin (PHA) results in increased synthesis and release of Ach as well as an increase in mRNA encoding for nAchR and mAchR (Kawashima and Fujii, 2000; Fujii and Kawashima, 2001) and suggests an autocrine and/or paracrine function for Ach in the regulation of immune function (Fujii and Kawashima, 2001). Inhibition of Concanavalin-A (Con A) induced T cell proliferation is blocked by the nAchR antagonist mecamylamine (MEC) and by acute nicotine exposure (Singh et al., 2000). Acute nicotine exposure of ConA stimulated mouse splenocytes resulted in decreased production of IL-10 and also resulted in increased production of IFN-gamma (Hallquist et al., 2000). The presence of human lymphocyte cell surface nAchR's has been determined by the binding of fluoresceine isothiocyanate (FITC)-conjugated $\alpha$-BTX; affinity purification of $\alpha$-BTX bound protein indicated that the nAchR bound were the same as those found in muscle (Toyabe et al., 1997). Others have determined the binding of $^3$H-nicotine to human PBMC indicating the presence of nAchR on the surface with a calculated density of ~2000 sites/cell (Grabczewska et al., 1990). Additionally the binding of $^3$H-nicotine to human neutrophils, monocytes and lymphocytes (Davies et al., 1982) has been determined. The formation of E-rosettes, a function of T cells from peripheral blood, and a method used for T cell enumeration, is decreased by 30%-40% with carbamylcholine chloride, a cholinergic antagonist, indicating the expression of nAchR on at least a subset of human T cells (Mizuno et al., 1982).

Clearly T-cell functions can be influenced by anticholinergics including peptide neurotoxins, an important aspect in autoimmune diseases. Including the inhibition of viral replication in immune cells, and viral inhibition even in the absence of acetylcholine receptors, and reported use of modified venoms in patients with rheumatoid arthritis (Montsedeoca et al, 1987) may suggest a general use in immune system disorders. The study of hydrogen peroxide-treated cobratoxin in EAE has confirmed the above observations. A decrease in mononuclear cuffing and diminished signs and symptoms associated with the induced disease was observed. It also provided evidence for the safe application of this specific venom component to the treatment of an autoimmune disorder.

The conversion of neurotoxins with hydrogen peroxide is relatively simple and can be achieved at relatively high protein concentrations (10 mg/ml). The reactive species is inexpensive and abundant. The reaction procedure with hydrogen peroxide occurs over the course of several days but factors such as the nature of protein being detoxified, protein and chemical concentrations in addition to pH and temperature conditions influence the rate of the reaction. Miller's studies (1977) have shown that with continued oxidation, the loss of the tryptophan residue can be observed. This coincides with the method for following the reaction of neurotoxins with ozone (Chang et al, 1990, Mundschenk, U.S. Pat. No. 5,989,857). Studies conducted by Miller suggest that the loss of toxicity may be due to the reduction in the number of disulphide bonds.

Alpha-neurotoxin solution, i.e., cobratoxin, is filter sterilized to remove bacteria. It can be dissolved in saline and made up to final volume minus $H_2O_2$ volume (see Sanders, U.S. Pat. No. 3,888,977). $H_2O_2$ should be added last while agitating. The final product is 10 mg/ml. The protein level can be increased concomitant with an increase in the level of $H_2O_2$ to yield 20 or 30 mg/ml solutions. There is a 1000 fold molar excess of $H_2O_2$ relative to neurotoxin. This increases production while keeping the handling volume to a minimum. The solution needs to be diluted prior to filling and administration (e.g. to 500 mcg/ml). Any suitable preservative for parenteral administration can be employed such as methyl paraben, benzalkonium chloride or metacreosol. For oral administration of the neurotoxin the modified protein must be combined with benzalkonium chloride at a protein:detergent ratio of between 1:6 to 1:8, and preferably 1:7.5 for solutions with modified cobratoxin.

The normal dosage of the present modified neurotoxin for the average adult is approximately 0.3 mg per day. The dosages are correspondingly adjusted for younger or older patients of greater or less body weight. The maximum dosage need not exceed 1 mg per day. Dosages of 0.03 mg have been found to be effective though with slower onset of relief. While a patient may be given the modified neurotoxin as infrequently as every other week, it is preferred that the composition be administered at least weekly, and preferably every other day or daily. The composition may be administered orally, subcutaneously, intramuscularly or intravenously. Parenterally, either subcutaneous or intramuscular injection is preferred. While the correct formulation with benzalkonium chloride will permit oral administration through absorption through the oral mucosa (preferably sublingually), this formulation may also permit administration otically. Furthermore transdermal delivery may be effected if formulated in an appropriate cream or lotion base using benzalkonium chloride as a permeation enhancer.

EXAMPLE 1

Inhibition of Acute Onset EAE

For the study female Lewis rats were divided into groups of 12 rats each. Two groups received subcutaneous injection of 200 μg guinea pig myelin basic protein (MBP) plus complete Freund's adjuvant (CFA) and treated with either modified cobratoxin or modified cobra venom. The control group received only subcutaneous injection of 200 μg guinea pig myelin basic protein (MBP) plus complete Freund's adjuvant (CFA). An acute phase study was run for 28 days post EAE induction.

All treated animals were receiving the treatment as three doses per week for three weeks prior to EAE induction. Each single dose of modified cobratoxin or cobra venom was 0.2 mg and was given subcutaneously.

All animals were examined for behavioral deficits daily. The examinations were by two individuals who were blinded as to the injections they received.

Pender Scores as follow:
Score 0 No Symptoms
Score 1 Tail Weakness
Score 2 Tail Paralysis
Score 3 Hind limb weakness
Score 4 Forelimb Weakness
Score 5 Hind limb Paralysis
Score 6 Forelimb Paralysis For tissue examination, each animal was sacrificed under perfusion with saline and Halothane anesthesia. Spinal cord and brain tissues fixed in formalin and embedded in paraffin, sectioned in 2-4 micrometer in thickness. The section stained with Hematoxylene and Eosin and examined using light microscope for the presence of perivascular lymphocyte infiltrate inflammation and graded as no inflammation, mild, moderate and severe as described by (Mohamed, 2004).

Figure 2:
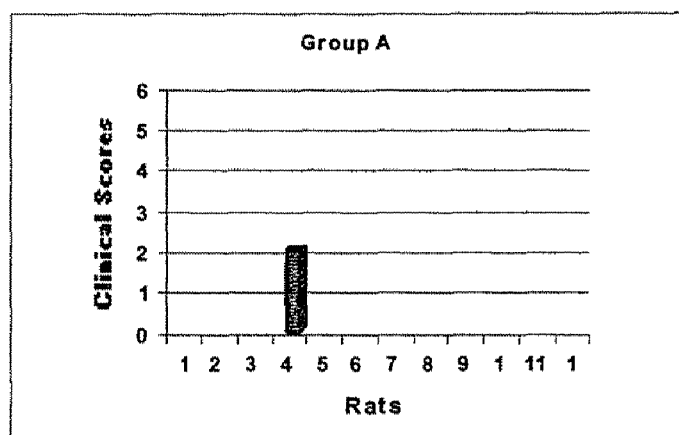
FIG. 2 is a bar graph showing clinical scores achieved by individual rats in Group A (Acute Phase) after EAE induction along with modified cobratoxin.
Figure 3:
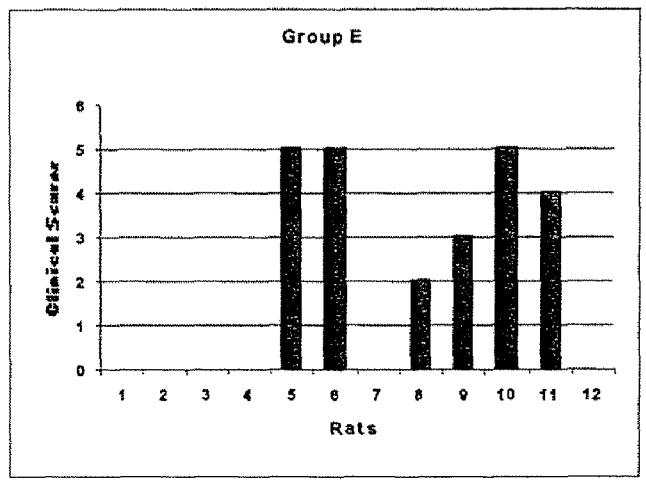
FIG. 3 is a bar graph showing clinical scores achieved by individual rats in Group E (Acute Phase) after EAE induction along with modified cobra venom.
Figure 7:
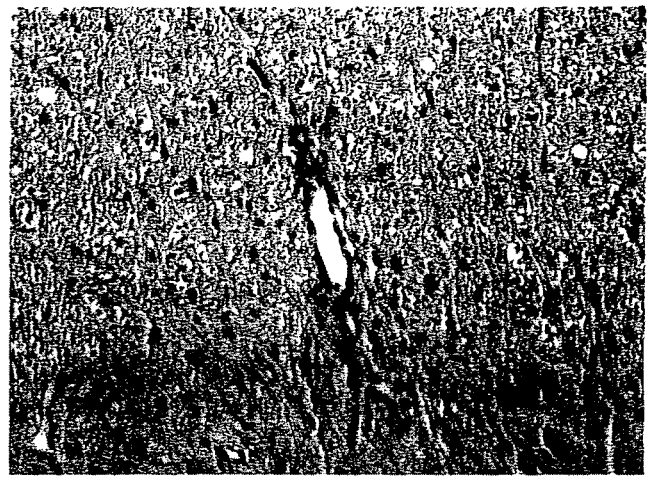
FIG. 7 is a graphical representation of a spinal cord with mild perivascular inflammation.

All control animals were symptomatic at 11-24 days. See FIG. 1. At the 28$^{th}$ day all had been sacrificed and perfusion fixed. Histological examination shows no signs of perivascular cuffing in all of modified cobratoxin group except one animal, who clinically was sick (FIG. 2), and showed mild perivascular cuffing in the spinal section (FIG. 7). The modified cobra venom group showed no signs of perivascular cuffing in six animals and those animals that were clinically sick (FIG. 3) and showed mild to moderate perivascular cuffing in the spinal and brain sections.

EXAMPLE 2

Inhibition of Chronic EAE

For the study female Lewis rats were divided into groups of 12 rats each. Two groups received subcutaneous injection of 200 μg guinea pig myelin basic protein (MBP) plus complete Freund's adjuvant (CFA) and treated with either modified cobratoxin or modified cobra venom. The control group received subcutaneous injection of 200 μg guinea pig myelin basic protein (MBP) plus complete Freund's adjuvant (CFA) used as a control animal models of EAE for the acute and relapsing stages respectively. A chronic phase study was run for 70 days post EAE induction.

Figure 4:
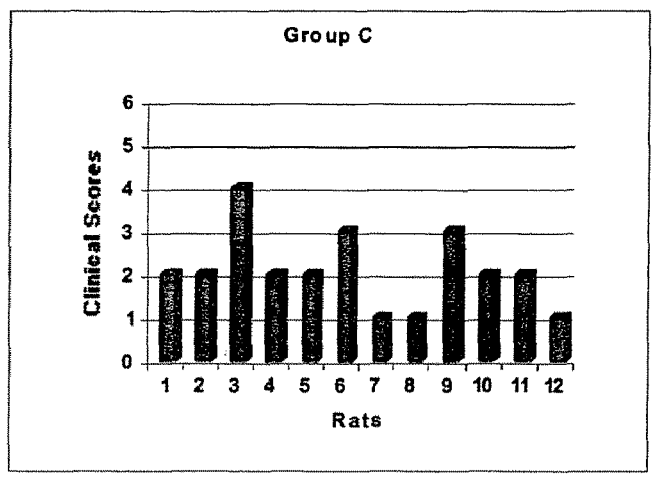
FIG. 4 is a bar graph showing clinical scores achieved by individual control rats in Group C (Chronic Phase) after EAE induction.
Figure 5:
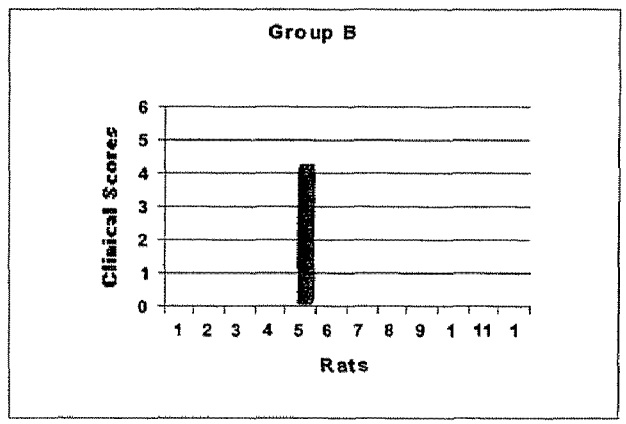
FIG. 5 is a bar graph showing clinical scores achieved by individual rats in Group B (Chronic Phase) after EAE induction along with modified cobratoxin.
Figure 6:
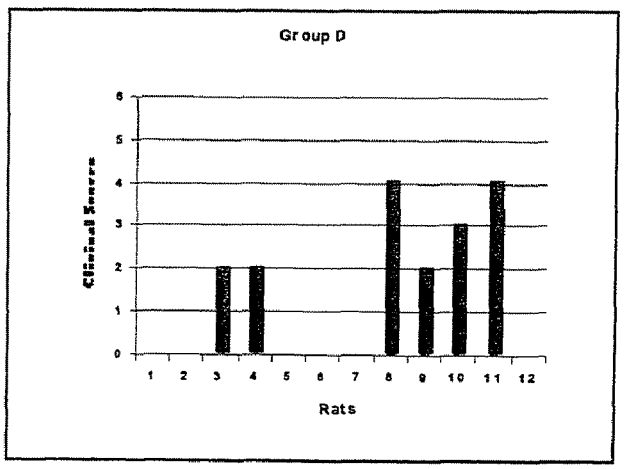
FIG. 6 is a bar graph showing clinical scores achieved by individual rats in Group D (Chronic Phase) after EAE induction along with modified cobra venom.

All control animals were symptomatic at 11-24 days. See FIG. 4. Animals were maintained on 0.2 ml of a drug once a week for the next five weeks. Animals were examined for behavioral deficits and weighed twice a day by two individuals. One animal showed symptoms day 7 to 20 when treated with modified cobratoxin (FIG. 5) whereas six animals showed symptoms day 11 to 27, when treated with modified cobra venom (FIG. 6).

Figure 8:
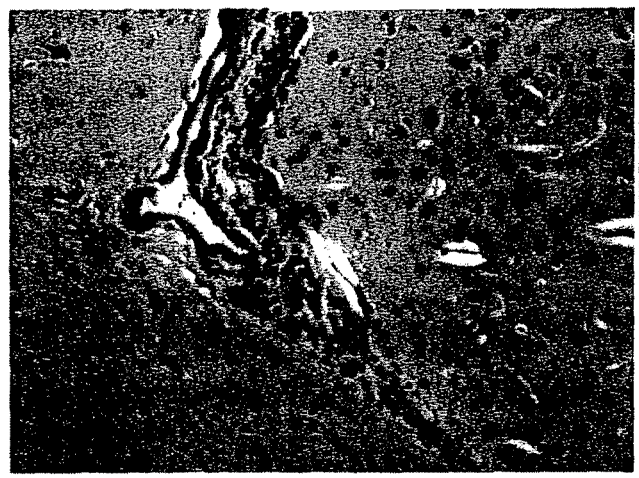
FIG. 8 is a graphical representation of a control group spinal cord with severe perivascular inflammation.
Figure 9:
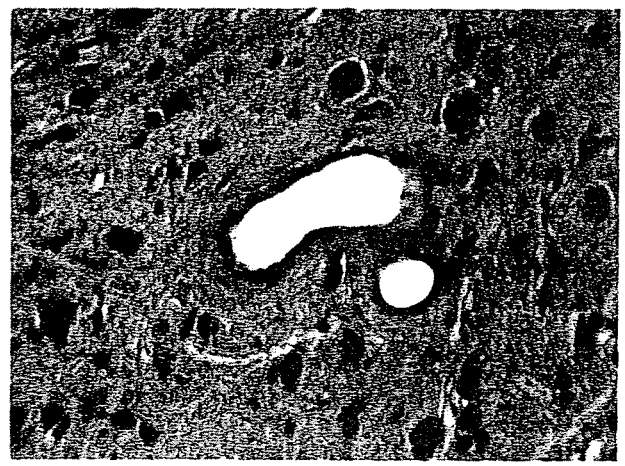
FIG. 9 is a graphical representation of the normal appearance of a spinal cord section containing normal blood vessels.

Histological examination at day 70 revealed six animals with no inflammation and six animals showed different degrees of perivascular inflammation from the modified venom group. In the modified cobratoxin group histological examination revealed only one animal with severe perivascular inflammation (FIG. 8) relative to normal tissue (FIG. 9).

The ability of hydrogen peroxide-modified cobratoxin to prevent the onset of EAE in rats in both acute and chronic experiments suggests that the drug could be effective in the amelioration of immune damage in autoimmune diseases with special emphasis to multiple sclerosis. Histological examination of the brains of the test animals shows a clear reduction in the numbers of lymphocytes recruited to areas of expected inflammation in comparison to controls. It suggests that the drug can render these immune cells non-responsive to the stimulation of antigen mixed with adjuvant. Furthermore the purified cobratoxin product is superior to the whole venom product in the prevention of disease contrary to the observations made in antiviral studies. Cobratoxin represents 15-20% of Naja naja kaouthia venom and so it could be concluded that the venom results reflect a cobratoxin low-dose response.

While the invention has been described, and disclosed in various terms or certain embodiments or modifications which it has assumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

What is claimed is:

1. A method of treatment of a human patient suffering from multiple sclerosis comprising administering to the patient a disease-mitigating amount of a composition consisting of an oxidatively detoxified and modified alpha-cobratoxin protein in a saline solution, wherein the toxicity of the modified alpha-cobratoxin protein is reduced at least 400-fold as compared with that of a native alpha-cobratoxin protein, and the disease-mitigating amount is a dosage in the range of 0.03-0.3 mg per day of the modified alpha-cobratoxin.

2. The method of claim 1 wherein the dosage of the composition is delivered in a volume substantially from 0.05 to 10 ml based on a 0.1% saline solution of said modified alpha-cobratoxin per 150 lbs body weight.

3. The method of claim 2 wherein the volume of the dosage is substantially from 0.2 to 2 ml.

4. The method of claim 2 wherein the dosage is administered substantially in a frequency of from every other week to daily.

5. The method of claim 2 wherein the dosage is administered substantially at least weekly.

6. The method of claim 2 wherein the dosage is administered substantially at least daily.

7. The method of claim 2 wherein the administration is by at least one of subcutaneous, intramuscular and intravenous injection, orally, otically and by intradermal routes.

* * * * *